(12) United States Patent
Williams et al.

(10) Patent No.: US 9,079,768 B2
(45) Date of Patent: Jul. 14, 2015

(54) DEHYDROGENATION OF AMMONIA-BORANE BY BIFUNCTIONAL CATALYSTS

(75) Inventors: Travis J. Williams, Los Angeles, CA (US); Brian L. Conley, Manhattan Beach, CA (US)

(73) Assignee: University of Southern California, Los Angeles, CA (US)

( * ) Notice: Subject to any disclaimer, the term of this patent is extended or adjusted under 35 U.S.C. 154(b) by 535 days.

(21) Appl. No.: 13/368,720

(22) Filed: Feb. 8, 2012

(65) Prior Publication Data

US 2012/0201744 A1    Aug. 9, 2012

Related U.S. Application Data

(60) Provisional application No. 61/440,544, filed on Feb. 8, 2011.

(51) Int. Cl.
*C01B 3/04* (2006.01)
*C07F 17/02* (2006.01)
*C07F 17/00* (2006.01)
*C07F 19/00* (2006.01)

(52) U.S. Cl.
CPC . *C01B 3/04* (2013.01); *C07F 17/00* (2013.01); *C07F 17/02* (2013.01); *C07F 19/005* (2013.01); *Y02E 60/364* (2013.01)

(58) Field of Classification Search
CPC .. C01B 6/10–6/13; C01B 35/146; C01B 3/06
See application file for complete search history.

(56) References Cited

PUBLICATIONS

Blaquiere et al. "Ruthenium-Catalyzed Dehydrogenation of Ammonia Boranes", Oct. 2008, J. Am. Chem. Soc. 130, 14034-14035.*
Conley et al. "Thermochemistry and Molecular Structure of a Remarkable Agostic Interaction in a Heterobifunctional Ruthenium—Boron Complex", Jan. 2010, J. Am. Chem. Soc. 132, 764-1765.*
Conley et al. "Discovery, Applications, and Catalytic Mechanisms of Shvo's Catalyst", Jan. 2010, Chem. Rev, 110, 2294-2312.*
Casey, C.P. et al., "Hydrogen Elimination from a Hydroxycyclopentadienyl Ruthenium(II) Hydride: Study of Hydrogen Activation in a Ligand-Metal Bifunctional Hydrogenation Catalyst," J. Am. Chem. Soc. 2005, 127, pp. 3100-3109.

* cited by examiner

*Primary Examiner* — Stanley Silverman
*Assistant Examiner* — Syed Iqbal
(74) *Attorney, Agent, or Firm* — Brooks Kushman P.C.

(57) ABSTRACT

Ligand-metal bifunctional ruthenium complexes are efficient catalysts for the liberation of two or more molar equivalents of hydrogen from ammonia-borane, a prospective hydrogen storage medium. In some cases, the mechanism for the dehydrogenation features a ruthenium hydride resting state from which dihydrogen loss is the rate-determining step.

20 Claims, 11 Drawing Sheets

DEHYDROGENATION OF AMMONIA-BORANE BY BIFUNCTIONAL CATALYSTS

CROSS-REFERENCE TO RELATED APPLICATIONS

This application claims the benefit of U.S. provisional application Ser. No. 61/440,544 filed Feb. 8, 2011, the disclosure of which is hereby incorporated in its entirety by reference herein.

TECHNICAL FIELD

The fields to which the disclosure generally relates include hydrogen storage, chemical catalysis and to methods of releasing hydrogen from ammonia-borane

BACKGROUND

The utility of hydrogen as a transportation fuel is limited by safety and practicality concerns involving pressurized gas in a mobile vehicle. Thus, a practical hydrogen storage system paired with an efficient fuel cell can enable hydrogen as an alternative to liquid transportation fuels. One conceptual solution is to store hydrogen in small molecules such as $MgH_2$, methanol, a hydrocarbon, or a boron-nitrogen compound. Particularly, ammonia-borane (AB, $NH_3BH_3$) is a promising material due to its high hydrogen content (19.6 wt %) and capacity to dehydrogenate under mild conditions. Several reports of transition metal catalyzed AB dehydrogenation have recently appeared. These involve rhodium, iridium, ruthenium, and nickel catalysts, among others. Among homogeneous systems, only Baker's $Ni(NHC)_2$ catalysts have achieved both high productivity (>2.5 equivalents $H_2$) and a useful rate (>$10^{-3}$ $s^{-1}$ at 60° C.).

Accordingly, there is a need for improved catalyst systems for dehydrogenating small molecules that store hydrogen.

SUMMARY OF THE INVENTION

The present invention solves one or more problems of the prior art by providing in at least one embodiment a method of releasing hydrogen from ammonia borane. The method comprises contacting ammonia borane with a compound having formula 1 such that hydrogen is released:

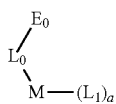
(1)

wherein
M is a transition metal;
$E_o$ is a moiety capable of accepting electrons;
$L_o$ is a linking ligand or moiety bonded to $E_o$ wherein $L_0$ includes a moiety that interacts with M with the proviso that when M is ruthenium, the moiety is not nitrogen in a primary or secondary amine;
$L_1$ are each independently ligands associated with M, each $L_1$ are the same or different; and
a is an integer from 1 to 6. Advantageously, the method of the present invention releases greater than 1 molar equivalent of hydrogen from ammonia borane.

In another embodiment of the present invention, a catalyst comprising a compound having the following formula is provided:

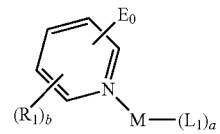
(7)

wherein
M is a transition metal;
$E_o$ is a moiety capable of accepting electrons; and
$L_1$ are each independently ligands associated with M, each $L_1$ are the same or different;
a is an integer from 1 to 6;
$R_1$ is hydrogen, $C_{1-8}$ alkyl, chlorine, bromine, fluorine, or OH; and
b is an integer from 0 to 5.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

DETAILED DESCRIPTION OF THE PREFERRED EMBODIMENT(S)

Figure 1:
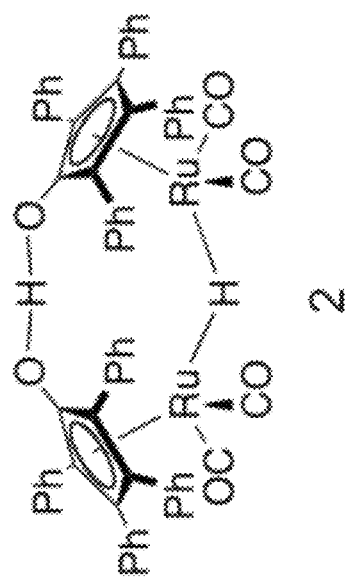
FIG. 1 provides Scheme 1 which illustrates dehydrogenation of AB with Shvo's Catalyst 1.
Figure 1:
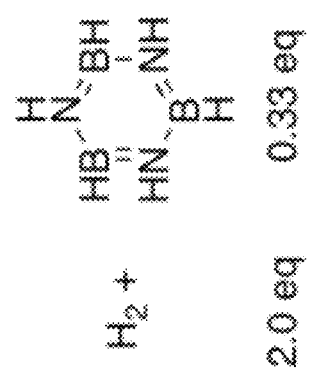

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

In an embodiment of the present invention, a method of releasing hydrogen from ammonia borane ("AB") is provided. The method comprising contacting ammonia borane with a compound having formula 1 such that hydrogen is released:

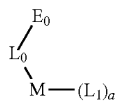
(1)

wherein
M is a metal, and in particular a transition metal;
$E_o$ is a moiety capable of accepting electrons;
$L_o$ is a linking ligand or moiety bonded to $E_0$ wherein $L_0$ includes a moiety that interacts with M with the proviso that when M is ruthenium, the moiety is not nitrogen in a primary or secondary amine;
$L_1$ are each independently ligands associated with M, each $L_1$ are the same or different; and
a is an integer from 1 to 6. In a refinement, a is an integer from 1 to 5. It should be appreciated that if the catalyst structure given by formula 1 is charged (typically, positively) there are a sufficient number of counter-ions to maintain overall charge neutrality. For example, when the metal complex is positively charged (e.g., 1+, 2+, etc.), the counter-ion may be represented by $X^-$ where $X^-$ is halide (e.g., chloride, bromide, iodide), $TfO^-$, and the like where TfO is trifluoromethanesulfonate. Counter-ions with multiple negative charges are also contemplated.

In a variation, the method further comprises collecting the hydrogen released from ammonia borane. Typically, $L_o$ has electron density that is capable of interacting with M. In one refinement $L_0$ derives this electron density from the lone pair of electrons from a heteroatom such as nitrogen. In another refinement, $L_0$ includes an aryl group that can interact with M. It should also be appreciated that many variations of formula (I) include an aryl group and a heteroatoms with the heteroatom interacting with M. In another variation, when $L_0$ interacts via a nitrogen atom and when M is ruthenium, the nitrogen atom is not in the form of a primary or secondary amine. In a further refinement of this variation, the nitrogen atom is $sp^2$ hybridized.

In a refinement, E is boron, hydrogen, or a hydrogen bond donor or acceptor. In another refinement, M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, gold, thallium, platinum lead, bismuth, polonium, thorium, protactinium, uranium, neptunium, and plutonium. In a further refinement, M is a transition metal selected from the group consisting of ruthenium, rhodium, iridium, and iron.

In a variation of the present embodiment, $L_1$ are each independently selected from the group consisting of neutral two electron donor ligands, anionic two electron donor ligands, pi-donor ligands, multidentate ligands, and monodentate ligands. In a refinement, the $L_1$ are each independently selected from the group consisting of carbon dioxide, halide, hydride, nitrate, hydroxide, acetonitrile, pyridine, ammonia, aquo, boryl, and combinations thereof. Similarly, in a variation of the present embodiment, $L_0$ is selected from the group consisting of neutral two electron donor ligands, anionic two electron donor ligands, pi-donor ligands, multidentate ligands, and monodentate ligands.

Typically, the reaction of the complex having formula 1 with ammonia borane is carried out in non-reactive aprotic solvents. Examples of such solvents include, but are not limited to, ethers, polyethers, and hydrocarbons. Specific examples include diglyme, triglyme, tetraglyme, and the like. In a refinement, the ammonia borane is present in the solvent in a concentration from about 0.05 to 5 moles/liter. In another refinement, the ammonia borane is present in the solvent in a concentration from about 0.1 to 2 moles/liter. In yet another refinement, the ammonia borane is present in the solvent in a concentration from about 0.2 to 1 moles/liter. In another refinement, the complex having formula 1 is present in an amount from about 0.5 to 15 mole percent (i.e., percent relative to ammonia borane). In another refinement, the complex having formula 1 is present in an amount from about 1 to 10 mole percent. In another refinement, the complex having formula 1 is present in an amount from about 2 to 5 mole percent.

In a variation of the present embodiment, the compound having formula 1 is described by formula 2:

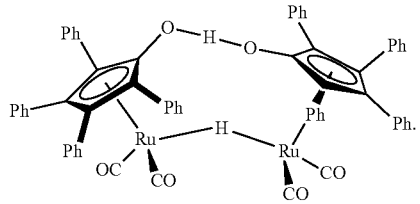

(2)

In another variation of the present embodiment, the compound having formula 1 is described by formula 3:

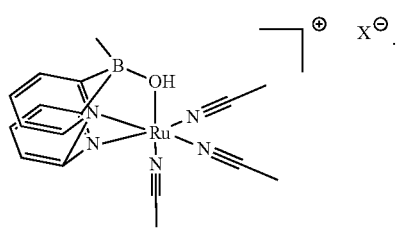

(3)

Note, the angle with the positive charge indicates the charge on the metal complex to the left $X^-$ is the counter-ion. For example $X^-$ may be halide (e.g., chloride, bromide, iodide), TfO$^-$, and the like where TfO is trifluoromethanesulfonate.

In still another variation of the present embodiment, the compound having formula 1 is described by formula 4:

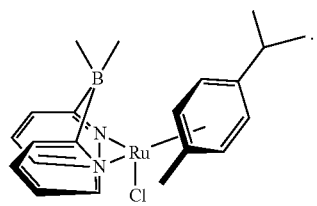

(4)

In still another variation of the present embodiment, the compound having formula 1 is described by formula 5:

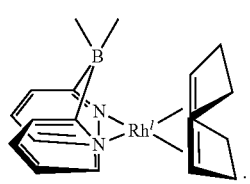

(5)

In yet another variation of the present embodiment, the compound having formula 1 is described by formula 6:

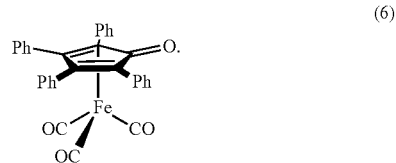

(6)

In another embodiment of the present invention, a catalyst comprising a compound having the formula 7 is provided:

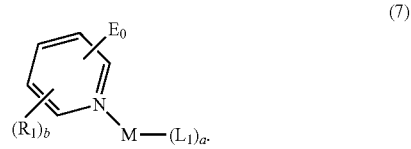

(7)

wherein

M is a metal, and in particular a transition;

$E_o$ is a moiety capable of accepting electrons; and $L_1$ are each independently ligands associated with M, each $L_1$ are the same or different;

a is an integer from 1 to 6;

$R_1$ is hydrogen, $C_{1-8}$ alkyl, chlorine, bromine, fluorine, or OH; and b is an integer from 0 to 5.

In a refinement of the present invention, $E_0$ is boron, hydrogen, or a hydrogen bond donor or acceptor. In another refinement, M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thulium, ytterbium, lutetium, hafnium, tantalum, tungsten, rhenium, osmium, iridium, gold, thallium, lead, bismuth, polonium, thorium, platinum, protactinium, uranium, neptunium, and plutonium. In a further refinement, M is a transition metal selected from the group consisting of ruthenium, rhodium, iridium, and iron.

In a variation of the present embodiment, $L_1$ are each independently selected from the group consisting of neutral two electron donor ligands, anionic two electron donor ligands, pi-donor ligands, multidentate ligands, and monodentate ligands. In a refinement, the $L_1$ are each independently selected from the group consisting of carbon dioxide, halide, hydride, nitrate, hydroxide, acetonitrile, pyridine, ammonia, aquo, boryl, and combinations thereof. Similarly, in a variation of the present embodiment, $L_0$ is selected from the group consisting of neutral two electron donor ligands, anionic two electron donor ligands, pi-donor ligands, multidentate ligands, and monodentate ligands.

In a refinement of the present embodiment, the catalyst has formula 8:

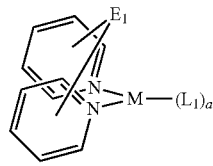

(8)

wherein $E_1$ is a moiety capable of accepting electrons and $L_1$ and a are as above.

Example 1

Reduction Using Shvo's Catalyst 7

Shvo's catalyst (i.e., compound having formula 2, Scheme 1, FIG. 1) enables liberation of 2.0 equivalents of $H_2$ from AB. Under certain conditions, this reaction is complete in 2 hours at 70° C. Equally interesting as this reactivity are the mechanistic data for the reaction. These indicate a kinetic regime previously unseen for the compound having formula 2 and are consistent with a bifunctional mechanism featuring release of $NH_2BH_2$ and dehydrogenation of the resulting intermediate(s).

Figure 2A:
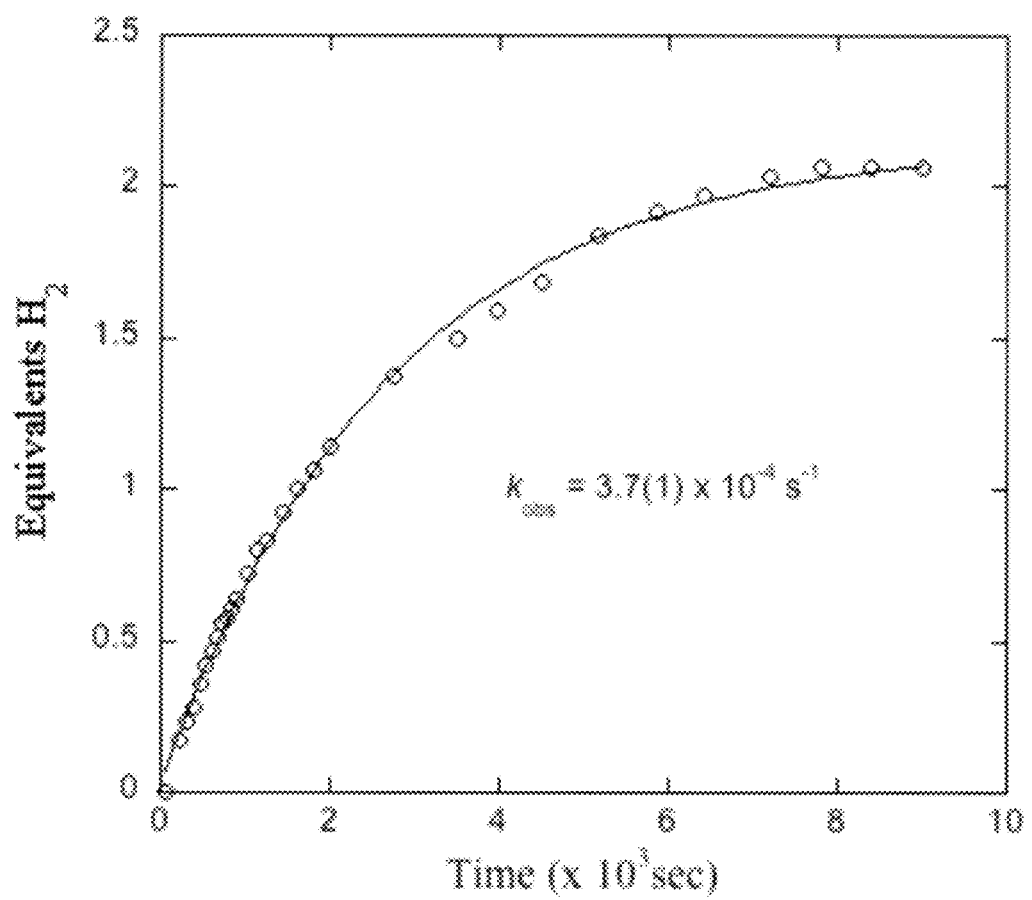
FIG. 2A provides eudiometer data showing production of hydrogen gas in the presence of 5.0 mol % catalyst 2 and 2.0 mol % ethanol in 2:1 diglyme/benzene at 70° C.

Catalytic reactivity of the compound having formula 2 with AB in a 2:1 diglyme/benzene solution in a sealed reactor proceeds at 70° C. The solution changes color from bright orange to yellow/brown and evolves hydrogen pressure in the reaction vessel. Hydrogen gas evolution (quantified by a eudiometer) and $^1H$ or $^{11}B$ NMR are effective tools to monitor the reaction. Under optimized conditions the reaction of 5.0 mol of the compound having formula 2 and 2.0 mol % ethanol (vide infra) with AB (0.42 M) liberated 1.0 equivalent hydrogen in 30 minutes and reached full conversion after 120 minutes to yield 2.0 equivalents hydrogen gas (FIG. 2A) when run in a reaction vessel open to a eudiometer. The presence of elemental mercury did not influence conversion for the reaction. The $^{11}B$ NMR spectrum of this solution at completion revealed borazine as the exclusive boron product. This indicates that cross-linking to form polyborazylene (PB) is not efficient under these conditions.

The mechanisms involved in AB dehydrogenation were investigated using $^1H$ and $^{11}B$ NMR spectroscopy. The reaction of 5.0 mol % of the compound having formula 2 with AB in diglyme/benzene-$d_6$ was investigated. Surprisingly, over several hours at room temperature disappearance of the metal μ-hydride resonance of the compound having formula 2 (−18 ppm) and appearance of a signal at −10 ppm, which is consistent with the formation of ruthenium hydride 9 are observed. This rapid rate of dimer dissociation is notable, given the reported barrier to dissociation of 28.8 kcal mol$^{-1}$ in toluene. Analysis of the $^{11}B$ spectrum several hours after the disappearance of the compound having formula 2 was complete did not reveal catalytic conversion of AB. However, upon heating to 70° C., the disappearance of AB is observed along with formation of several boron-containing species, including cyclic trimer 12 and borazine in the $^{11}B$ spectrum. Notably, $^{11}B$ NMR analysis at early times (through ca. 30% conversion) reveals that the most prominent boron containing species is borazine. At the same time, a smaller resonance at −11 ppm is observed. This overlaps with the —$BH_2$ group of 12 as it grows into solution and is most likely 12's unbranched isomer, cyclotriborazane.

Figure 2B:
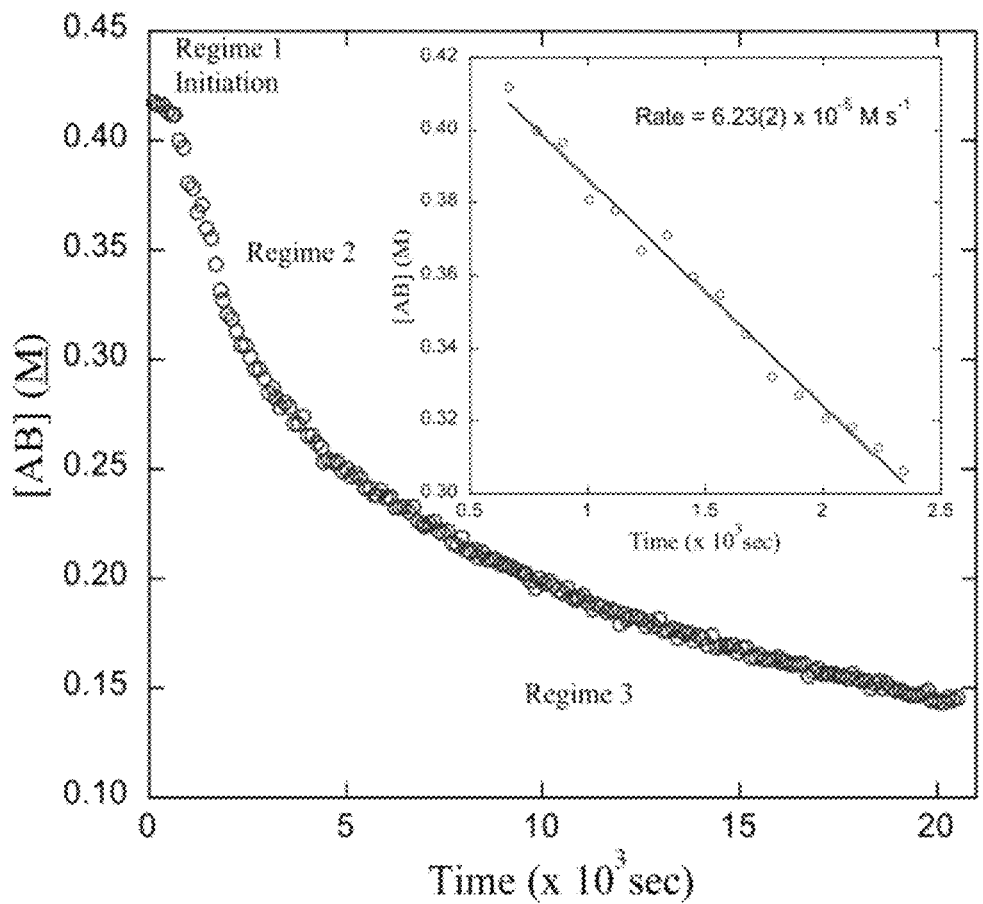
FIG. 2B provides $^{11}B$ NMR data showing consumption of AB in the presence of 2.5 mol % catalyst 2 in a sealed J. Young NMR tube.

A kinetic profile for AB consumption was generated by plotting [AB] against time (FIG. 2B). The data features three rate regimes: 1. a brief initiation period (ca. 2% conversion), 2. a fast linear regime (through ca. 30% conversion), and 3. a slower regime that fits to first order exponential decay.

The kinetics of the initiation period (regime 1) were studied by $^1H$ NMR and are consistent with dissociation of 2 to 9 and 10 followed by rapid reduction of 10 to 9 by AB. Interestingly, there is zero order in [AB] for this process while [2] is first order, which suggests that dissociation of the dimer is rate limiting in catalyst initiation and that AB is uninvolved in the rate determining step.

Regime 2 was of particular interest because the plot of [AB] vs. time was linear with a sharp slope and eudiometer measurements at corresponding times showed rapid $H_2$ evolution. Indeed, calculations suggest that the rate of hydrogen production in regime 2 (eudiometry) is comparable to AB loss ($^{11}B$ NMR integration) with rates of $6.1 \times 10^{-8}$ M s$^{-1}$ and $7.9 \times 10^{-8}$ M s$^{-1}$ respectively. Varying the catalyst concentration allowed for the comparison of regime 2 rate values determined from the slope of this linear region. A ln(Rate)/ln [2] plot reveals a linear relationship with a slope of 0.96, which indicates a first order dependence on [Ru]. This contrasts cases of 2-catalyzed aldehyde hydrogenation and alcohol oxidation which have half-order dependence on [Ru]. In AB dehydrogenation, this regime is changed by the very rapid reduction of 10 to 9, which makes dehydrogenation of 9 rate-determining. Kinetics and NMR data support the presence of a persistent ruthenium hydride throughout the reaction and indicate that a monomeric hydride (such as 9 or a closely related species) is the resting state of the catalyst. Interestingly, as the reaction proceeds into regime 3, the hydride region of the $^1H$ NMR spectrum contains at least three distinct resonances within 0.5 ppm of the originally derived hydride compound at −10 ppm. This indicates conversion of 9 to related compounds as the concentration of dehydrogenated products increases, potentially accounting for the observed loss in rate.

Figure 3:
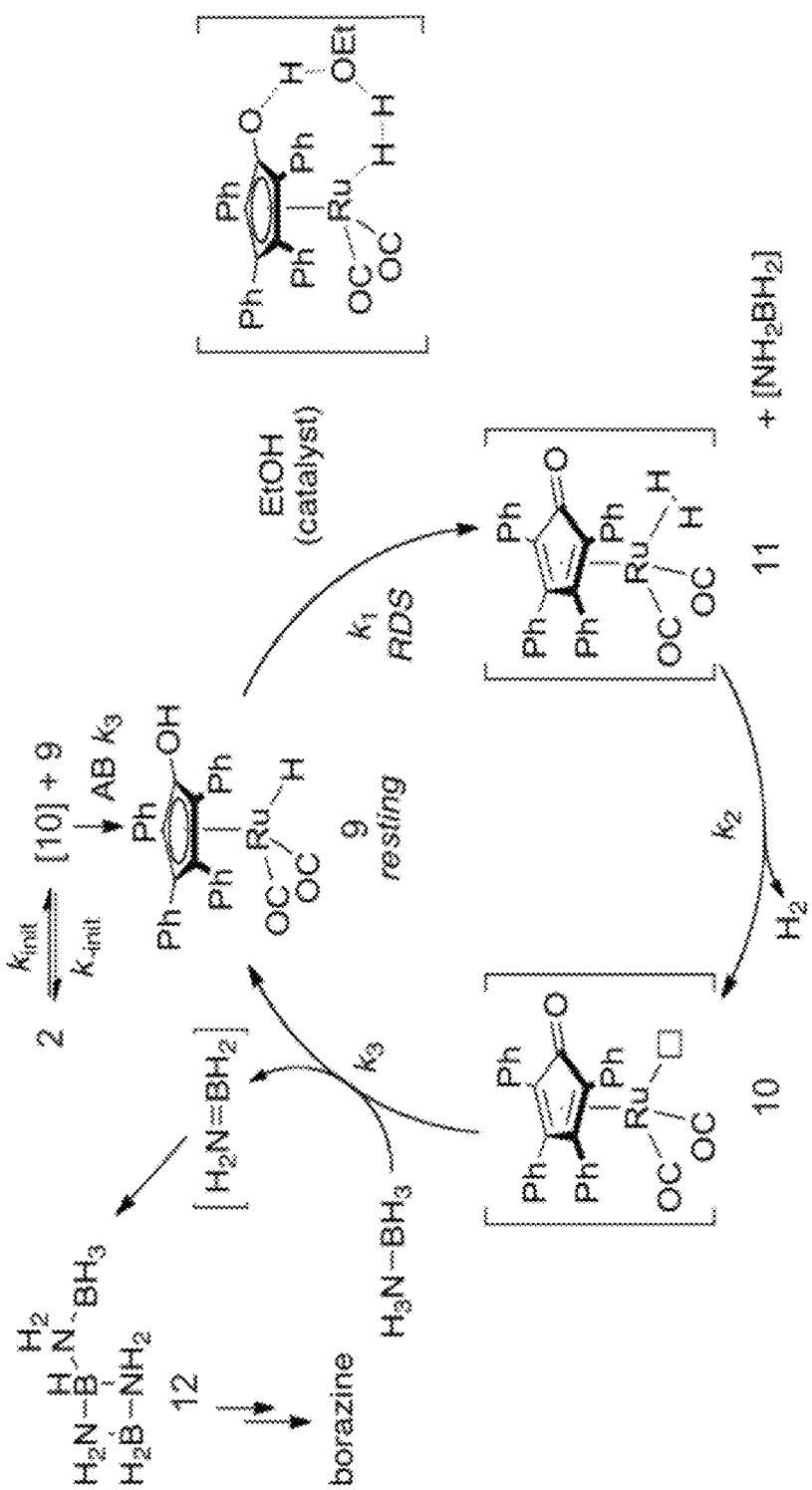
FIG. 3 provides Scheme 2 which is a proposed mechanism for catalysis in Regime 2. Rate=$2k_1[1][EtOH]$.

It is observed that the reaction was significantly faster in deoxygenated, bench top grade diglyme than under anhydrous conditions. Along these lines, it was found that adding ethanol to anhydrous diglyme/benzene increased the reaction rate: the kinetics experiment was repeated in the presence of various catalytic quantities of ethanol in rigorously anhydrous reaction solutions containing AB and 5.0 mol % 2. A linear dependence of $k_{obs}$ on concentration from 0 to 17.0 mole percent was observed, which is consistent with Casey's finding that added alcohol catalyzes the release of hydrogen from a tolyl-analogue of 9 by shuttling the ligand hydroxyl proton to the Ru—H to form a labile dihydrogen complex (11, Scheme 2, FIG. 3). (C. P. Casey, J. B. Johnson, S. W. Singer, Q. Cui, J. Am. Chem. Soc. 2005, 127, 3100-3109.)

The possibility of stepwise mechanisms involving oxidative addition of the B—H bond to 10 or successive deprotonation/hydride transfer cannot be excluded, a concerted, outer sphere pathway for proton and hydride transfer to 10 is favored. Unfortunately, the rapid rate of $k_3$ relative to dihydrogen loss from 9 ($k_1$) precludes measurement of kinetic isotope effects for $k_3$ under catalytic conditions.

It is believed that the third regime in the $^{11}B$ NMR kinetics arises due to the build-up of products other than $H_2$ that slow catalysis. In a reaction run under $D_2$ pressure (50 psig, 3.4 atm), deuterium is not incorporated into AB or the dehydrogenated products as monitored by $^2H$ NMR. Further, the kinetic profile of this reaction matches the reaction run under 1 atm $N_2$. These observations indicate that dehydrogenation is irreversible under these conditions and that rate inhibition is not related to increased $H_2$ pressure. However, a reaction run with 1 equivalent added borazine shows significant differences in its kinetic profile. Under these conditions, there is also a short initiation period followed by slow catalysis that fits a first order exponential decay model. Thus, it is proposed that the catalysis slows gradually in the presence of borazine. However, when more AB is added to spent reaction solutions, an increase in rate of AB loss through 3 successive catalytic runs is observed, even as the borazine concentration builds in the sealed NMR tube. The increased rate coincides with a change in product distribution.

In summary, an efficient system for catalytic dehydrogenation of ammonia-borane that liberates two equivalents of hydrogen and gives borazine as the by-product has been described in this example. This is the second example of a homogeneous transition metal catalyst that liberates more than one equivalent of hydrogen gas from AB itself. Data and literature precedent leads to the mechanistic proposal in Scheme 2 for regime 2, the initial mechanism of ammonia-borane dehydrogenation with the compound having formula 2. Pre-catalyst 2 undergoes first order dissociation ($k_{init}$, [AB] order is zero) to give 9 and 10; the latter is rapidly reduced to 9 by AB. Complex 9 is the resting state of the cycle; ethanol-catalyzed dihydrogen loss from 9 ($k_1$) is rate determining, where $k_1$ is first order in [Ru] and dependant on [ROH]. This presumably proceeds through the intermediacy of a ruthenium dihydrogen complex (11) to give the postulated oxidizing species 10 as Casey has shown. The situation that $k_1$ is rate-determining in a catalytic system is a previously unobserved regime for the compound having formula 2. A concerted, bifunctional transition state for B—H and N—H transfer in the conversion of 10 to 9 is protected, but remains speculative.

Example 2

Ruthenium Catalyst for Dehydrogenation of Ammonia Borane

Figure 4:
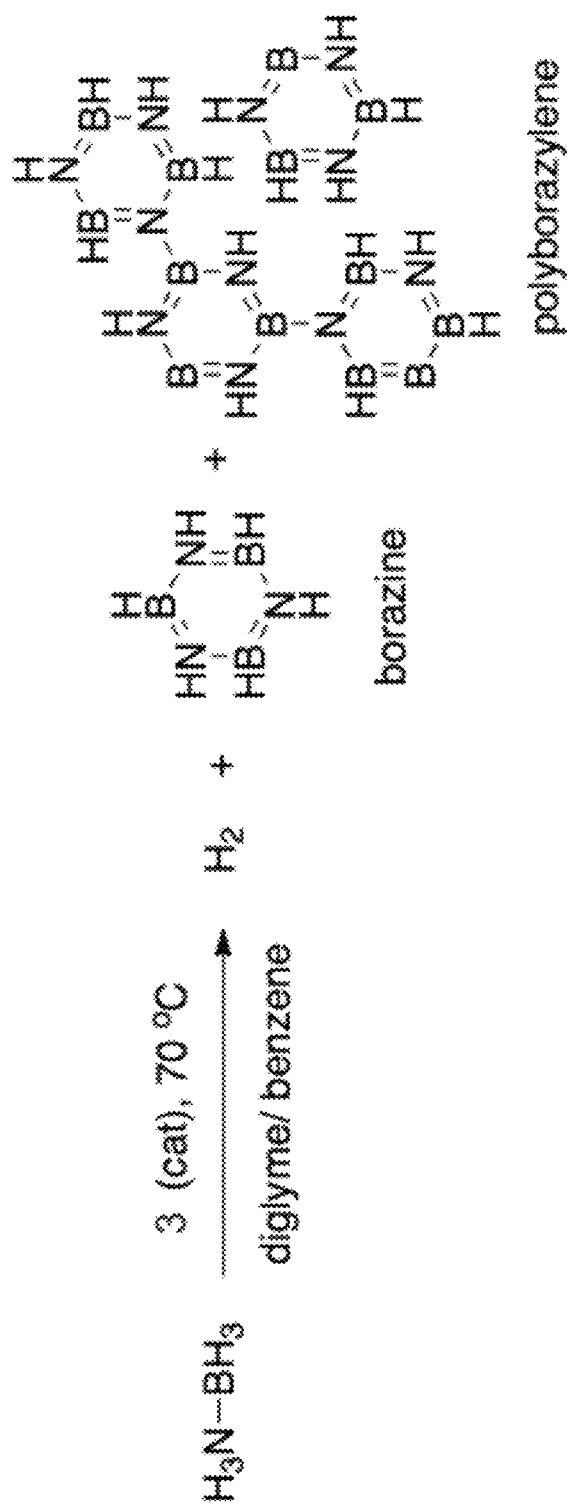
FIG. 4 provides Scheme 3 showing dehydrogenation of ammonia borane to produce hydrogen, borazine, and polyborazylene.

The catalyst having formula 3 liberates $H_2$ from ammonia borane (AB) under air in diglyme solutions (FIG. 4, Scheme 3):

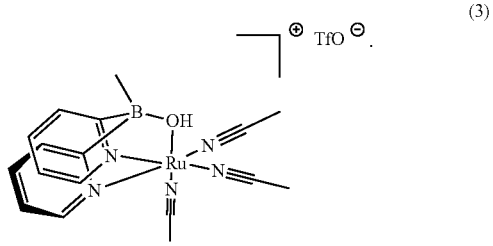
(3)

Figure 5:
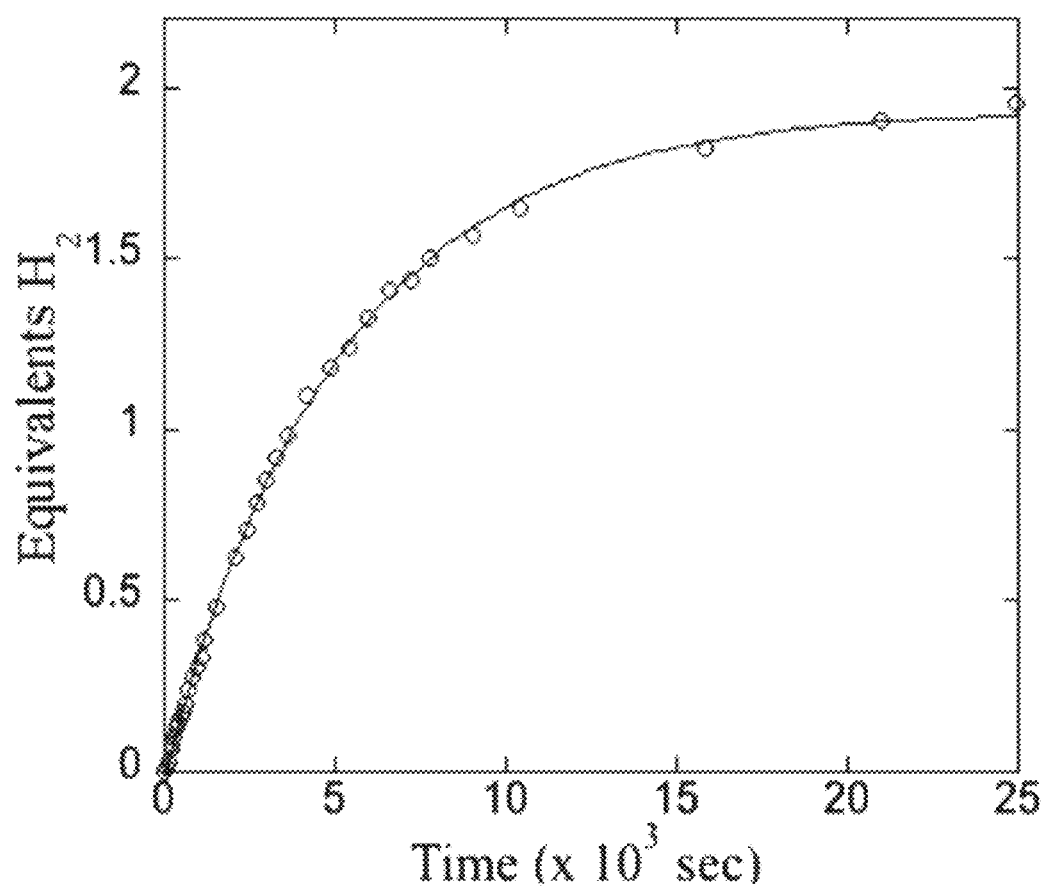
FIG. 5 provides eudiometer data showing production of hydrogen gas from AB in the presence of 5.0 mol % catalyst 3 under air at 70° C. in 11:1 diglyme/benzene solution.
Figure 6:
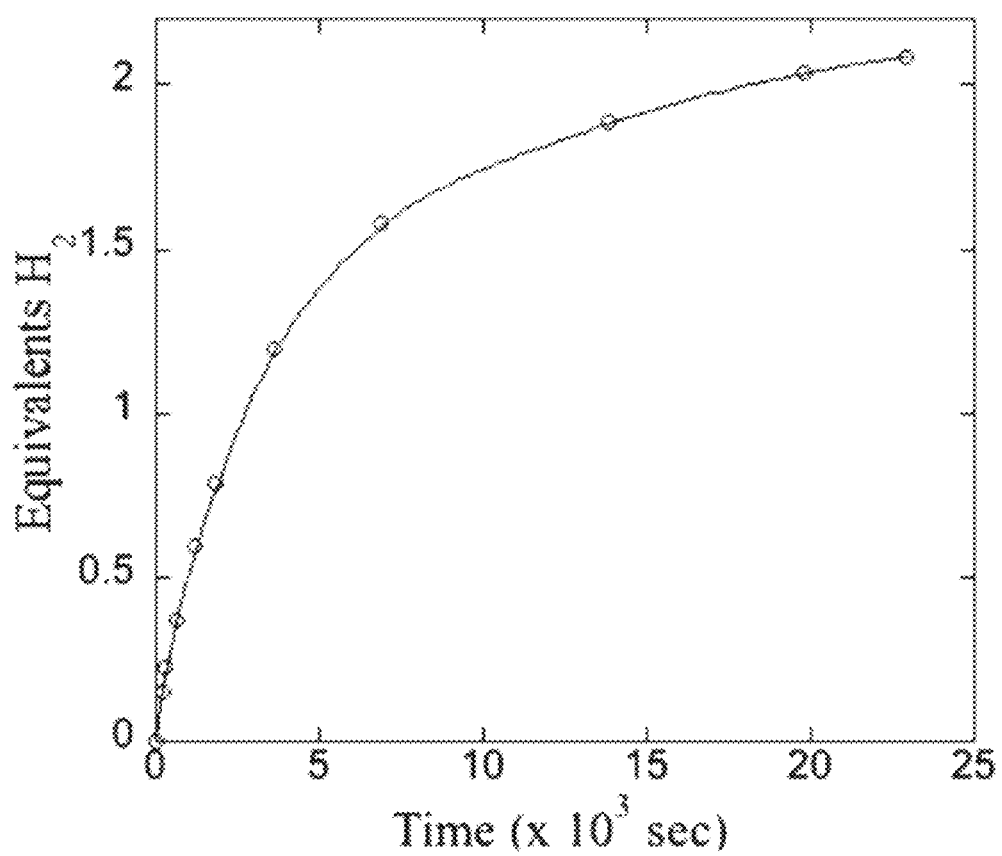
FIG. 6 provides eudiometer data showing production of hydrogen gas from AB in the presence of 2.0 mol % catalyst 3 in tetraglyme under air at 70° C. at high [AB] ($H_2$ release=4.2 system wt %)

The efficiency of AB dehydrogenation with the catalyst having formula 3 is evaluated by treating a 0.42M AB solution with 5.0 mol % 1 at 70° C. in a Schlenk flask under air and monitoring the production of $H_2$ using a eudiometer. The system produced 1.94 equiv of $H_2$ in 7 hours (FIG. 5). Added metallic mercury did not inhibit the reaction under these conditions thereby indicating homogeneous catalysis. More practical, highly concentrated suspension conditions have also been examined. A slurry of AB and tetraglyme (100.0 mg of AB, 202.6 mg of tetraglyme, 5.8 system wt % stored $H_2$) was treated with 2.0 mol % 1 at 70° C. and yielded 2.0 equiv of $H_2$ in 4 hours and a total of 2.2 equiv (turn over number ("TON")=110) upon completion of the reaction. This corresponds to the release of 4.2 wt % $H_2$. In contrast, uncatalyzed AB dehydrogenation liberates only 1.6 equiv of $H_2$ at 70° C. at a rate that is about 2.5-fold slower under similar reaction conditions.

The catalyst system of the present example is also remarkably reusable. Data for successive runs at 2.0 mol % loading (70° C.) indicate that the catalysis is efficient through four runs of approximately 6 hours at high AB concentration, although the reaction slurry did become viscous. To help alleviate this situation, 0.2 mL of tetraglyme were added while recharging the reactor with AB for subsequent runs. In this way, four successive runs were performed in a single reactor. The rates for all of these were similar, and they released 2.2, 2.1, 2.3, and 2.2 equiv of $H_2$, respectively, for a total TON of 440. With a catalyst loading of 0.1 mol %, we observed a TON of about 5700 over three runs and liberation of up to 4.6 wt % $H_2$. For comparison, Fagnou reported a ruthenium catalyst that could release up to 1.0 system wt % $H_2$ from AB at room temperature and up to 3.6 system wt % $H_2$ from AB/MeNH$_2$BH$_3$ mixtures at 50° C. This is the best previously published weight-content $H_2$ release for a homogeneous catalytic system dehydrogenating an amine-borane.

The catalyst system of the present example works well when open to air, which is beneficial for commercialization since a system stable to air and water provides practical advantages over a more sensitive one. Measurements of $H_2$ produced in eudiometry studies in air and under $N_2$ were identical under concentrated AB conditions. To quantify this effect further, rate constants ($k_{obs}$) for [AB] consumption obtained for reactions conducted under nitrogen and air were compared. In this experiment, 2.5 mol % 1 was prepared in diglyme/benzene-d$_6$ in a glovebox and sonicated open to air for 1 hour prior to addition of AB to ensure removal of the $N_2$ environment and establish atmospheric $O_2$ levels in the NMR tube. The $k_{obs}$ values at 70° C. were $2.65(9) \times 10^{-4}$ s$^{-1}$ in air and $2.54(9) \times 10^{-4}$ s$^{-1}$ in $N_2$. Neither inhibition nor acceleration of the catalysis is observed. This suggests that at ambient levels of $O_2$, the catalysis is not shut down by decomposition of the active species or accelerated by formation of a more reactive, higher-valent ruthenium oxo complex.

The mechanism of AB dehydrogenation was probed with the catalyst having formula 3 by $^{11}$B NMR spectroscopy in dilute diglyme solutions. Unlike Shvo's catalyst, the catalyst having formula 3 demonstrates first-order kinetics in [AB] through 3 half-lives, as observed by the disappearance of the AB resonance in the 11B NMR spectrum. Consistent with prior art observations, the intermediates observed in these reactions are branched and unbranched cyclotriborazane, aminoborane oligomers, borazine, and polyborazylene ("PB"), with the latter two being the major products upon completion. As is the case for Shvo's catalyst, the formation of insoluble B, N oligomers is not observed in this system.

The appearance of PB at early times in reactions with the catalyst having formula 3 is encouraging, whereas none is seen under Shvo conditions. Formation of PB is a feature of extensive dehydrogenation, indicating the production of more than 2 equiv of $H_2$, and it has been proposed to occur by borazine cross-linking in transition-metal-catalyzed systems. However, in contrast to (NHC)Ni systems, in which borazine is quickly consumed, [borazine] increases over time in reactions of the catalyst having formula 3 and is not consumed late in the reaction. This suggests that catalytic borazine cross-linking is not the mechanism for PB formation in this system. The operative mechanism is suspected to involve reaction of borazine with AB or one of its early dehydrogenation products. Efficient catalytic borazine cross-linking has not been demonstrated to date in the absence of other B,N materials.

Rate data ($k_{obs}$, 70° C.) collected by $^{11}$B NMR spectroscopy were pseudo-first-order in AB. A catalyst order study was conducted by comparing the $k_{obs}$ values measured at various concentrations of the catalyst having formula 3. The data gave a linear plot of $\ln(k_{obs})$ versus $\ln([3])$ with a slope of 0.56, which indicates the presence of a dinuclear $(Ru)_2$ intermediate, 12 although this species was not observed. Possible structures include those containing a B—O—B bridge, a bridging hydride, or a product of AB dehydrogenation serving as the bridging moiety. Along these lines, a persistent metal hydride was not observed, which argues against a Ru—H moiety as the resting state of the catalyst. This is in line with observations of the (NHC)Ni systems but contrasts our own and others' findings for ruthenium, and iridium catalysts.

It is suspected that the catalyst having formula 3 might be analogous to several known catalysts that interact with the polarized B—H and N—H bonds of AB concurrently in a bifunctional transition state. This proposition was probed by recording deuterium isotope effects for isotopologues of AB. The $k_H/k_D$ values for the B—H and N—H bonds were 1.22 (14) and 1.58(9), respectively. A combined isotope effect measured using $D_3N$—$BD_3$ ($k_{NHBH}/k_{NDBD}$) was 1.67(18). Thus, the product of the two independently measured isotope effects [1.92(25)] is within experimental error of the measured double isotope effect, which is consistent with a concerted, asynchronous transition state in the rate-determining step. However, this conclusion is tentative because it is uncertain whether the observed isotope effects involve $H_2$ transfer from AB to the catalyst or multiple steps, as in the (NHC)Ni system.

Figure 7:
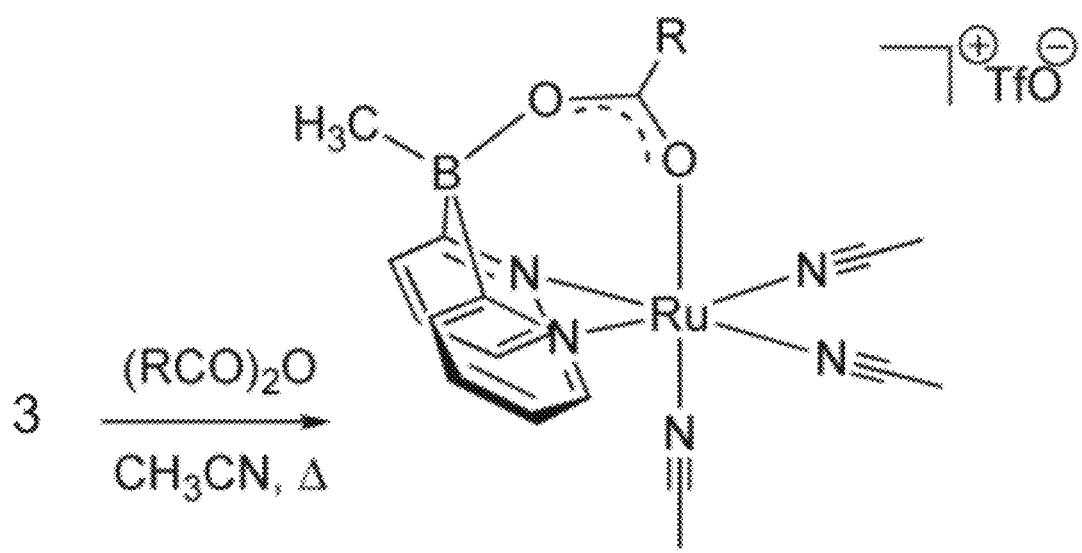
FIG. 7 provides Scheme 4 showing synthesis of bridging acetate complexes.

Other mechanistic scenarios have the bridging hydroxyl group of the catalyst having formula 3 donating $H^+$ to the solution, thus initiating an acid-catalyzed reaction, or the thus-formed oxide bridge providing an internal base in a bifunctional mechanism. To probe these, bridging carboxylate complexes 13 and 14 (Scheme 4, FIG. 7) were synthesized, which are devoid of the protic functionality. The crystal structure of 14 (FIG. 8) shows an unprecedented Ru—B $\mu_2$-kO:k O' bonding mode for the trifluoroacetate wherein the boron is distorted from its tetrahedral geometry to give a trigonalpyramidal structure. This behaviour could be rationalized by unfavorable steric interactions between the bridging carboxylate and other ligands in the unobserved $\mu_2$-kO:$^k$O (single bridging oxygen) mode. The same is suspected for 12.

Surprisingly, 5.0 mol % solutions of 3 and 13 have the same rate constant for AB consumption [$k_{obs}$=3.74(7)×10$^{-4}$ and 3.72(10)×10$^{-4}$ s$^{-1}$, respectively, at 70° C.]. This disfavors a H+-catalyzed mechanism. To interrogate the potential role of boron as a Lewis acid, AB dehydrogenation was attempted with complex 3, which has different electronic characteristics than 3 and 13. This gives faster catalysis: 2.5 mol % solutions of 3 and 14 gave rate constants of $k_{obs}$=2.66(12)×10$^{-4}$ and 5.77(12)×10$^{-4}$ s$^{-1}$, respectively, for AB consumption at 70° C. Thus, the occupancy of the bridging coordination site between Ru and B has an important influence on the dehydrogenation rate.

In multiple solvents it was observed that the acetate and trifluoroacetate complexes hydrolyze completely in the presence of trace water to re-form bridging hydroxide complex 3 and the corresponding carboxylic acid, which indicates a thermodynamic preference for the Ru(OH)B bridge. Adding water (ca. 6 equiv) to a sample of 3 in tetrahydrofuran-$d_8$ reveals that the hydrolysis has a half-life of 6-7 hours at room temperature, thus demonstrating the lability of the carboxylate ligand. Furthermore, a methylene chloride-$d_2$ solution of 3 and 1 equiv of TFA-$d_1$ showed the coalescence of the bound and free trifluoroacetic acid (TFA) signals at 50° C. as monitored by $^{19}$F NMR spectroscopy: two fluorine resonances [δ 75.38 (bound) and 75.25 (free) at 25 C] coalesced to one (δ 75.51). This observation indicates that exchange occurs rapidly on the NMR time scale. Thus, the bridging trifluoroacetate appears to be sufficiently labile to allow boron and ruthenium to participate in catalysis, but these data do not rule out participation of the acetate and trifluoroacetate in the mechanism of AB dehydrogenation by 13 and 14, as has been documented in systems for hydrocarbon CH activation.

Importantly, dehydrogenation is not efficient in the absence of the borate ligand. Catalyst 3's nonligated synthetic precursor, [(cym)RuCl$_2$]$_2$ (15), does not participate in efficient catalysis; these reactions precipitate metallic material under our experimental conditions. $^{11}$B NMR data for catalysis with 15 revealed a rate of AB consumption that is only about 2-fold lower than that of catalyst 3; however, $H_2$ production from this system was limited to 1 equiv, and it is not reusable. Additionally, added metallic mercury significantly attenuated the production of $H_2$ with catalyst 15.

This example demonstrates an efficient and robust catalyst for highly productive ammonia borane dehydrogenation. This catalyst liberates up to 4.6 wt % $H_2$ from AB suspensions and is resistant to deactivation in air. The catalyst's longevity at low catalyst loadings (TON up to 5700) and its air stability are unprecedented in transition metal-catalyzed AB dehydrogenation.

Example 3

Heterobifunctional Ruthenium-Boron Complex

Figure 8:
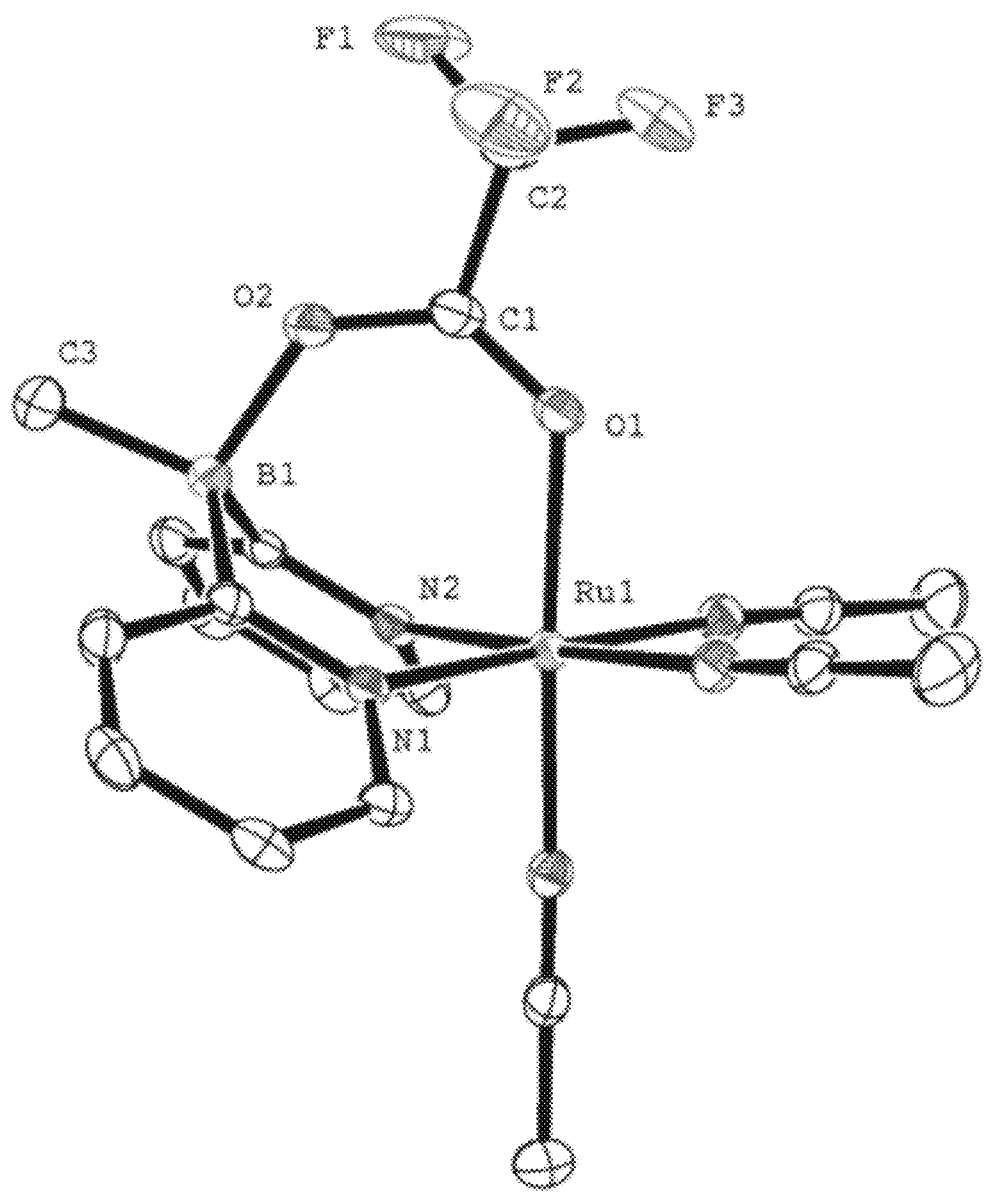
FIG. 8 provides an Oak Ridge Thermal Ellipsoid Plot Program ("ORTEP") plot of complex 14 with 50% probability ellipsoids (H atoms and the triflate counterion have been omitted for clarity)

The syntheses of agostic complex 20 and pre-catalyst 3 are outlined in Scheme 5 in FIG. 8. The route is initiated with the formation of chlororuthenium adduct 4 from 16 and 17. Treatment of 4 with AgOTf in acetonitrile-$d_3$ in a J. Young NMR tube affects rapid formation of 17 [1H δ(B-Me))+0.09, +0.04 ppm]; solvent then displaces cymene in minutes at elevated temperature to give an equilibrating mixture of 19 and 20 (1:1 at 90° C.), which can be hydrolyzed to give 3 [$^1$H δ(B-Me))+ 0.29 ppm].

The spectral data for complex 20 feature $^1$H resonances at +0.18 and −5.13 ppm (Δδ=5.3 ppm). While the downfield shift is consistent with bonding only at boron, the peak at −5.13 ppm is more consistent with an agostic interaction. In an attempt to arrest the agostic interaction, solutions of 19 and 20 were cooled to −40° C. in acetonitriled and −95° C. in dichloromethane-$d_2$. The upfield signal remained a singlet in each case, indicating rapid interconversion among the three hydrogens of the bridging methyl at these temperatures. A 25° C. HMBC spectrum of the equilibrating mixture elucidated the carbon chemical shifts of the boron-bound carbon atoms and illustrated that the upfield methyl group in 20 was bound both to boron (correlation to the other BMe $^{13}$C: 8 ppm) and ruthenium (correlation to acetonitrile ligands 13C: 125 ppm). The low 1JC-H values provide further evidence for an agostic interaction. Although $^1J_{C-H}$ values for the boron methyls of 19 and 20 could not be observed directly each was measured in a $^{13}$C-coupled HSQC experiment: $^1J_{C-H}$(agostic)) 100 Hz; $^1J_{C-H}$(free)) 107 Hz in 20. For comparison, 19 has $^1J_{C-H}$ (free)=109 Hz. The nearest examples of a metal-bound alkyl borate in the literature include a Pt(IV) case and a bis(pyrazolyl)diethylborate-ligated Mo(II) complex.

Figure 9:
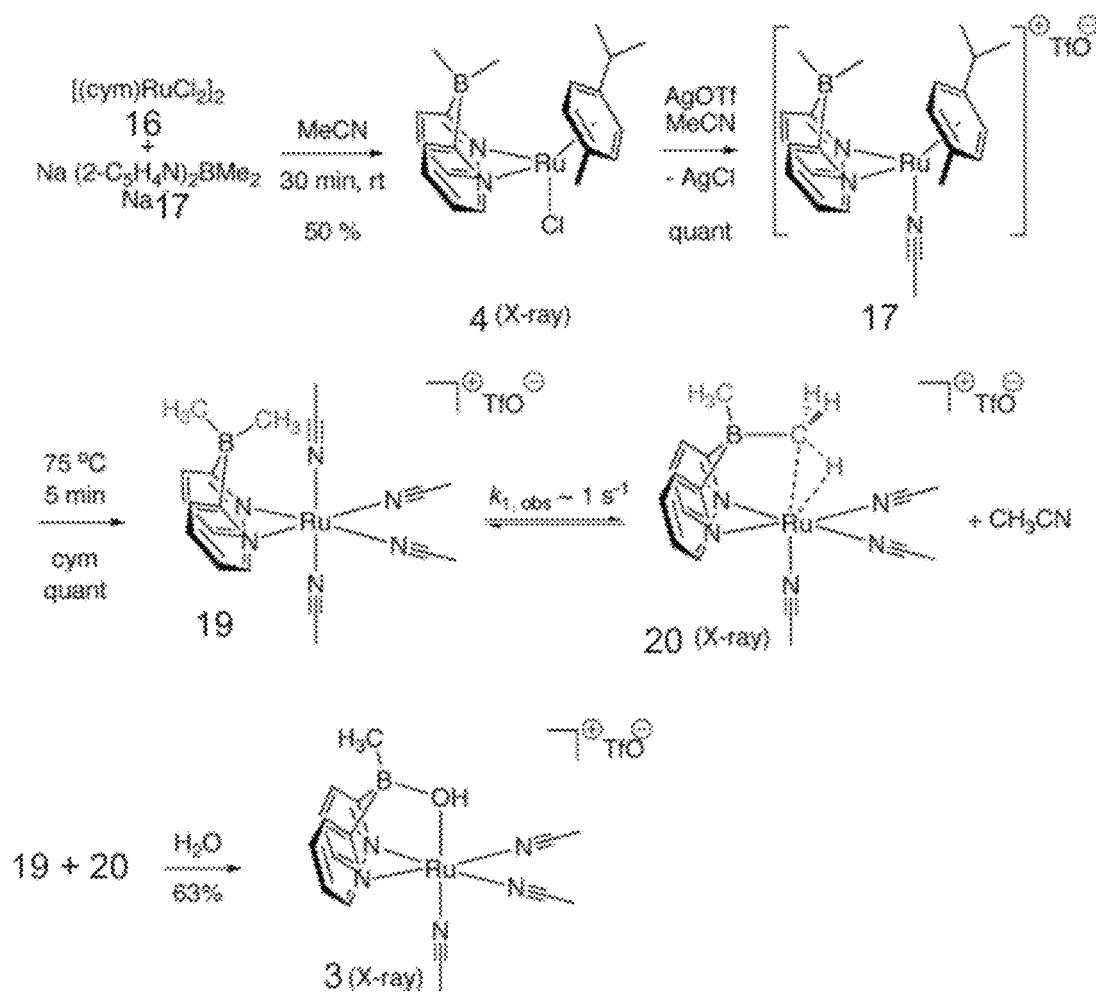
FIG. 9 provides Scheme 5 showing the synthesis of Bis(2-pyridyl)borate-ligated ruthenium complexes.

The NMR data for catalyst 20 show that the lifetimes of 19 and 20 are on the order of 1 second in solution, and [20]/[19]

decreases at lower temperature. Nonetheless, low-temperature vapor diffusion enabled crystallization of 20 in dichloromethane at low acetonitrile concentration. Remarkably, these crystals enabled collection of an X-ray structure that clearly defines the atomic connectivity in 20 (FIG. 9). A direct comparison of the X-ray structures of 3 and 20 illustrates the positions of the dipyridylborate ligand with an oxygen or agostic bridge (FIG. 9). The agostic C—H in 20 was positioned using the electron difference map. The Ru1-C1 bond distance of 2.53 Å in 20 is in contrast to the bond distance of 2.10 Å for Ru1-O1 in 3.

The thermochemistry for the equilibration of 19 and 20 was measured by NMR spectroscopy. This equilibrium has a linear van't Hoff plot from 20 to 80° C. with $\Delta H=5.5(2)$ kcal/mol and $\Delta S=20.1(5)$ eu. The conversion of 20 to 19 was conveniently studied by NMR magnetization transfer: at 85° C., bridge cleavage has $k_{-1,obs} \approx 1$ s−1. The mechanism for conversion of 20 to 19 has kinetic order with respect to [MeCN], which is consistent with a rapid preequilibrium followed by rate-determining acetonitrile association or concerted displacement of the agostic bond from 20. The microscopic reverse of this reaction involves the very rare situation that an agostic bond displaces a ligand from an 18-electron metal center. Determination of second-order rate constants k−1 by inversion-recovery enabled the determination of the activation parameters for cleavage of the agostic interaction, which were found to be $\Delta H_q=13.3(6)$ kcal/mol and $\Delta S_q=-27.5(43)$ eu using Eyring analysis over a range of 41° C.

Figure 10:
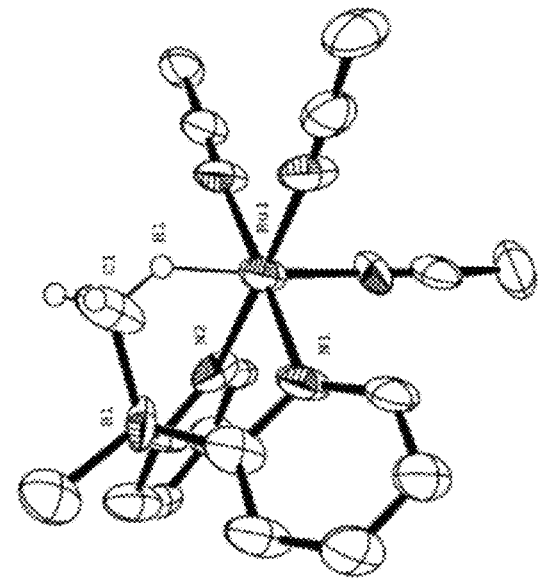
FIG. 10 provides ORTEP diagrams of complex 3 (left) and 20 (right) (Selected hydrogens and the counterions have been omitted for clarity. Ellipsoids are drawn at the 50% level. For comparison sake, the bond lengths (Å) for the agnostic BMe-M interactions in 7 and [(3)PtIVMe3] are Ru1-H1, 1.72; B1-C1, 1.66; Ru1-C1, 2.53; Ru1-B1, 2.89, and Pt1-H1, 2.02; B1-C1, 1.68; Pt1-C1, 2.76; Pt1-B1, 3.08, respectively).
Figure 10:
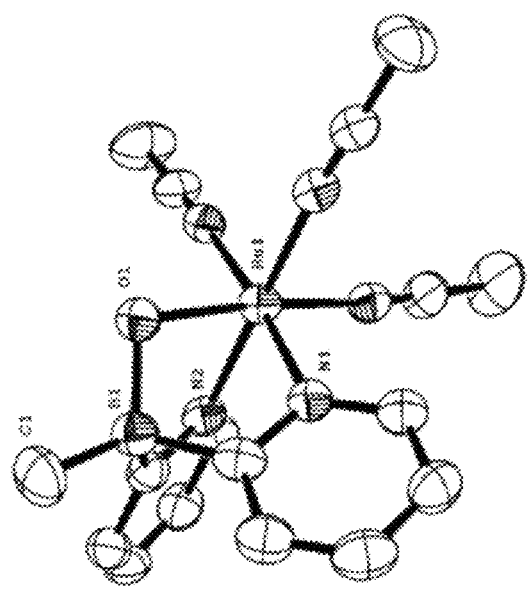

Complex 3 shows catalytic reactivity in the oxidation of p-methoxyphenethylalcohol (Scheme 7, FIG. 10). Heating 10 mol % 1 with alcohol and 40 mol % t-BuOK in acetone resulted in >95% yield of the corresponding ketone. The mechanism of this reaction is unknown.

In summary, we have reported here the first example of an agostic bridge between boron and ruthenium atoms. The structure of this agostic bridge was established by a combination of NMR and X-ray diffraction methods. Cleavage of the bridge has kinetic order with respect to acetonitrile concentration, indicating that bridge dissociation is either a rapid pre-equilibrium or concerted displacement. Thus, this is a very rare situation in which an agostic interaction is in equilibrium with a tightly binding ligand. A hydrolyzed form of this ligand-metal bifunctional complex is a catalyst for transfer dehydrogenation of alcohols, although the mechanism of this reaction has not been established.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of releasing hydrogen from ammonia borane, the method comprising:
    contacting ammonia borane with a compound having formula 1 such that hydrogen is released:

$$\begin{array}{c} E_0 \\ L_0 \\ M-(L_1)_a \end{array} \quad (1)$$

wherein
  M is a transition metal;
  $E_o$ is a moiety capable of accepting electrons;
  $L_o$ is a linking ligand or moiety bonded to $E_o$ wherein $L_0$ includes a moiety that interacts with M with the proviso that when M is ruthenium, the moiety is not nitrogen in a primary or secondary amine;
  $L_1$ are each independently ligands associated with M, each $L_1$ are the same or different; and
  a is an integer from 1 to 6.

2. The method of claim 1 wherein $E_0$ is boron, hydrogen, or a hydrogen bond donor or acceptor.

3. The method of claim 1 wherein a is an integer from 1 to 5.

4. The method of claim 1 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thulium, ytterbium, lutetium, hafnium, tantalum, tungsten, rhenium, osmium, iridium, gold, platinum, thallium, lead, bismuth, polonium, thorium, protactinium, uranium, neptunium, and plutonium.

5. The method of claim 1 wherein M is a transition metal selected from the group consisting of ruthenium, rhodium, iridium, and iron.

6. The method of claim 1 wherein the $L_1$ are each independently selected from the group consisting of neutral two electron donor ligands, anionic two electron donor ligands, pi-donor ligands, multidentate ligands, and monodentate ligands.

7. The method of claim 1 wherein the $L_1$ are each independently selected from the group consisting of carbon dioxide, halide, hydride, nitrate, hydroxide, acetonitrile, pyridine, ammonia, aquo, boryl, and combinations thereof.

8. The method of claim 1 wherein $L_0$ is selected from the group consisting of neutral two electron donor ligands, anionic two electron donor ligands, pi-donor ligands, multidentate ligands, and monodentate ligands.

9. The method of claim 1 wherein the compound having formula 1 is described by the following formula:

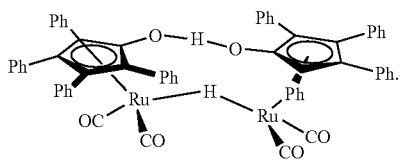

10. The method of claim 1 wherein the compound having formula 1 is described by the following formula:

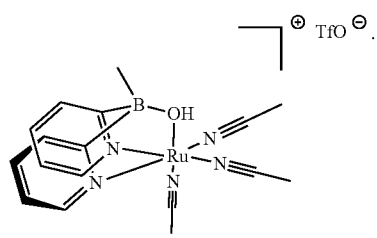

11. The method of claim 1 wherein the compound having formula 1 is described by the following formula:

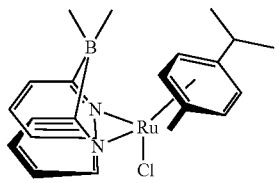

12. The method of claim 1 wherein the compound having formula 1 is described by the following formula:

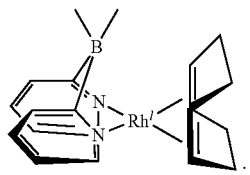

13. The method of claim 1 wherein the compound having formula 1 is described by the following formula:

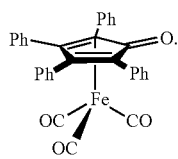

14. A catalyst comprising a compound having the following formula:

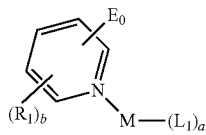

wherein
M is a transition metal;
$E_o$ is a moiety capable of accepting electrons; and
$L_1$ are each independently ligands associated with M, wherein at least one $L_1$ is selected from the group consisting of multidentate ligands, each $L_1$ are the same or different wherein at least one $L_1$ is a multidentate ligand; and
a is an integer from 1 to 6;
$R_1$ is hydrogen, $C_{1-8}$ alkyl, chlorine, bromine, fluorine, or OH; and
b is an integer from 0 to 5.

15. The catalyst of claim 14 wherein $E_0$ is boron, hydrogen, or a hydrogen bond donor or acceptor.

16. The catalyst of claim 14 wherein M is a metal selected from the group consisting of beryllium, magnesium, aluminum, scandium, titanium, vanadium, chromium, manganese, iron, cobalt, nickel, copper, zinc, gallium, germanium, yttrium, zirconium, niobium, molybdenum, technetium, ruthenium, rhodium, palladium, silver, cadmium, indium, tin, antimony, lanthanum, cerium, praseodymium, neodymium, promethium, samarium, europium, gadolimium, terbium, dysprosium, holmium, erbium, thulium, ytterbium, lutetium, hafnium, tantalum, tungsten, rhenium, osmium, iridium, gold, thallium, lead, bismuth, polonium, thorium, protactinium, uranium, neptunium, and plutonium.

17. The catalyst of claim 14 wherein M is a transition metal selected from the group consisting of ruthenium, rhodium, iridium, and iron.

18. The catalyst of claim 14 wherein the $L_1$ are each independently selected from the group consisting of neutral two electron donor ligands, anionic two electron donor ligands, pi-donor ligands, multidentate ligands, and monodentate ligands.

19. The catalyst of claim 14 wherein the $L_1$ are each independently selected from the group consisting of carbon dioxide, halide, hydride, nitrate, hydroxide, acetonitrile, pyridine, ammonia, aquo, boryl, and combinations thereof.

20. The catalyst of claim 14 having the following formula:

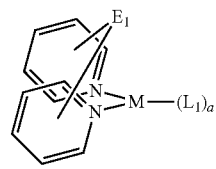

wherein $E_1$ is a moiety capable of accepting electrons.

* * * * *